United States Patent
Li et al.

(10) Patent No.: US 12,381,007 B2
(45) Date of Patent: Aug. 5, 2025

(54) PANCREATIC POSTOPERATIVE DIABETES PREDICTION SYSTEM BASED ON SUPERVISED DEEP SUBSPACE LEARNING

(71) Applicant: ZHEJIANG LAB, Hangzhou (CN)

(72) Inventors: Jingsong Li, Hangzhou (CN); Peijun Hu, Hangzhou (CN); Yu Tian, Hangzhou (CN); Tianshu Zhou, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 18/788,009

(22) Filed: Jul. 29, 2024

(65) Prior Publication Data
US 2024/0395408 A1  Nov. 28, 2024

Related U.S. Application Data

(63) Continuation of application No. PCT/CN2023/089985, filed on Apr. 23, 2023.

(30) Foreign Application Priority Data

Apr. 29, 2022 (CN) .......................... 202210466102.7

(51) Int. Cl.
*A61B 5/00* (2006.01)
*A61B 6/00* (2006.01)
(Continued)

(52) U.S. Cl.
CPC .............. *G16H 50/20* (2018.01); *A61B 6/50* (2013.01); *A61B 6/5217* (2013.01); *G06T 5/20* (2013.01);
(Continued)

(58) Field of Classification Search
CPC .......... A61B 6/032; A61B 6/5217; A61B 6/50
See application file for complete search history.

(56) References Cited

U.S. PATENT DOCUMENTS

2019/0019300 A1  1/2019 Simpson et al.
2021/0390686 A1  12/2021 Xu et al.

FOREIGN PATENT DOCUMENTS

CN    110047082 A    7/2019
CN    110599461 A    12/2019
(Continued)

OTHER PUBLICATIONS

International Search Report (PCT/CN2023/089985); Date of Mailing: Jul. 22, 2023.
(Continued)

*Primary Examiner* — Joel F Brutus
(74) *Attorney, Agent, or Firm* — Wiersch Law Group

(57) ABSTRACT

A pancreatic postoperative diabetes prediction system based on supervised deep subspace learning. A deep convolutional neural network and the MITK software are used to obtain postoperative residual pancreas area, so as to taken as the region-of-interest. Traditional image radiomics features and deep semantic features are extracted from the residual pancreas area, and a high-dimensional image feature set is constructed. Clinical factors related to diabetes, including pancreatic excision rate, fat and muscle tissue components, demographic information and living habits are extracted, and a clinical feature set is constructed. Based on a supervised deep subspace learning network, image and clinical features are represented and fused in subspace in dimensionality reduction, while a prediction model is trained to mine sensitive features highly relevant to the prediction risk of a patient suffering postoperative diabetes mellitus with a high degree of automation and discriminative accuracy.

8 Claims, 4 Drawing Sheets

(51) Int. Cl.
- *A61B 6/50* (2024.01)
- *G06T 5/20* (2006.01)
- *G06T 7/00* (2017.01)
- *G06T 7/11* (2017.01)
- *G06T 7/13* (2017.01)
- *G16H 50/20* (2018.01)
- *A61B 6/03* (2006.01)

(52) U.S. Cl.
CPC .............. *G06T 7/0016* (2013.01); *G06T 7/11* (2017.01); *G06T 7/13* (2017.01); *A61B 6/032* (2013.01); *G06T 2207/10081* (2013.01); *G06T 2207/20081* (2013.01); *G06T 2207/20084* (2013.01); *G06T 2207/20221* (2013.01); *G06T 2207/30092* (2013.01)

(56) References Cited

FOREIGN PATENT DOCUMENTS

| | | | |
|---|---|---|---|
| CN | 111915596 | A | 11/2020 |
| CN | 112164067 | A | 1/2021 |
| CN | 113113140 | A | 7/2021 |
| CN | 113160229 | A | 7/2021 |
| CN | 113284151 | A | 8/2021 |
| CN | 113570619 | A | 10/2021 |
| CN | 113870258 | A | 12/2021 |
| CN | 114565613 | A | 5/2022 |
| RU | 2313832 | C1 | 12/2007 |

OTHER PUBLICATIONS

First Office Action(CN202210466102.7); Date of Mailing: Jun. 15, 2022.

Notice Of Allowance(CN202210466102.7); Date of Mailing: Jul. 8, 2022.

Non-official-translation-Segmentation-Algorithm-based-on-Convolutional-Neural-Network-and-Variational-Pancreas-and-Cyst-thereof.

Multiscale-Receptive-Field-based-on-Residual-Network-for-Pancreassegmentation-in-CT-Images.

Application-of-artificial-intelligence-medical-imaging-technology-in-grading-of-pancreatic-neuroendocrine-neoplasms.

Automatic-Pancreas-Segmentation-in-CT-Images-With-Distance-Based-Saliency-Aware-DenseASPP-Network.

Deep-subspace-clustering-to-achieve-jointly-latent-feature-extraction-and-discriminative-learning.

PANCREATIC POSTOPERATIVE DIABETES PREDICTION SYSTEM BASED ON SUPERVISED DEEP SUBSPACE LEARNING

CROSS-REFERENCE TO RELATED APPLICATIONS

The present application is a continuation of International Application No. PCT/CN2023/089985, filed on Apr. 23, 2023, which claims priority to Chinese Application No. 202210466102.7, filed on Apr. 29, 2022, the contents of both of which are incorporated herein by reference in their entireties.

TECHNICAL FIELD

The present application relates to the technical field of medical and health information and, in particular, to a pancreatic postoperative diabetes prediction system based on supervised deep subspace learning.

BACKGROUND

Pancreas is an important organ that produces endocrine and exocrine hormones, which is crucial for glucose metabolism. Patients undergoing pancreatectomy are at risk of impaired glucose tolerance/diabetes mellitus (IGT/DM), with a reported incidence of 4.8%-60%, and the development of diabetes varies from 30 days to 3.5 years after the operation. The incidence rate is different due to the heterogeneity of the patient population, the decrease of the pancreatic parenchymal volume and the type of pancreatectomy. Distal pancreatectomy (DP) is a standard surgical treatment method, which is used to remove tumor and non-tumor lesions in the body and tail of pancreas. However, the related factors of new-onset diabetes after pancreatectomy are still unclear and have not been fully studied. Because a healthy lifestyle and timely medical intervention are considered to be effective ways to reduce the risk of diabetes, it is necessary and meaningful to predict the new-onset diabetes after pancreatectomy at an early stage. However, the literature on predicting new-onset diabetes after pancreatectomy is very limited, and the classification of diabetes based on image data is more challenging.

In a small amount of literature work, demographic information such as gender, age, BMI and laboratory indicators such as glucose tolerance and rapid blood sugar value are extracted based on electronic medical record data, and the risk factors of diabetes are mined. However, there is no research work to establish a risk prediction model using image data. As one of the routine imaging methods for pancreatic diseases, CT has the advantages of clear development and non-invasion, and CT images can reflect the texture of pancreas. It is of great significance and clinical application value to predict the risk of diabetes after pancreatectomy by combining basic clinical information and CT image features.

The existing diabetes risk prediction after pancreatectomy is generally based on electronic medical records by extracting demographic information such as age, gender, BMI, etc., laboratory data such as rapid blood glucose value, glucose tolerance, serum glycosylated hemoglobin, etc., and considering related factors such as pancreatic residual volume and pancreatic volume resection rate. The risk factors of diabetes are mined based on statistical test methods, but no risk prediction system is established. Among them, BMI is usually used to measure the degree of obesity as a risk factor for diabetes. But in fact, different fat and muscle components are very related to human metabolic diseases, which directly reflect the degree of obesity. At the same time, there is no method to predict the risk of diabetes after pancreatectomy by combining clinical information and imaging data. As for the radiomics prediction for other diseases, a disease prediction model is generally established by manually delineating the region of interest, calculating shallow image features such as texture, feature screening and machine learning model construction. However, it is time-consuming and labor-intensive to use this method to predict the risk after pancreatectomy, which requires the delineation of the region of interest on preoperative and postoperative CT. In the aspect of feature calculation and screening, generally only shallow image features are considered, and features are screened by statistical analysis or recursive feature elimination. Feature screening and classification models are independent of each other, which is not good for dimensionality reduction of high-dimensional features. In the construction of a classification model, traditional machine learning classification models such as logistic regression, support vector machine and random forest are generally selected, and the accuracy of diabetes risk prediction after pancreatectomy is not high enough.

SUMMARY

In view of the shortcomings of the prior art, the present application provides a diabetes risk prediction system after pancreatectomy based on supervised deep subspace learning by combining clinical and image features. The present application proposes to automatically segment the preoperative CT pancreatic region by using a deep convolutional neural network, and then simulate the pancreatic margin by using MITK software to obtain the postoperative pancreatic region, thus greatly reducing the workload of labeling the region of interest. The first-order statistics, shape and texture features of the wavelet filtered image are extracted from the residual pancreatic region, and then the high-level semantic feature of the postoperative pancreatic region is extracted by the deep convolutional neural network to construct an image feature set of the residual pancreatic region. Further, the related risk factors after pancreatectomy are extracted or calculated, including demographic information, living habits, resection rate of pancreatic volume, residual volume of pancreas and abdominal fat and muscle content, and a set of clinical features of pancreas is established. Then, a supervised deep subspace learning method is innovatively proposed to filter and fuse the image feature set and clinical feature set at the same time, and the sparse representation of them in the low-dimensional subspace is obtained, from which a similarity matrix between the data is calculated. Finally, based on the supervised module in the deep subspace learning network, the risk of postoperative diabetes is predicted. The present application can combine the clinical information of patients and high-dimensional image features, find low-dimensional features related to the postoperative diabetes risk through deep subspace learning, and predict the postoperative diabetes risk of patients at the same time, which has higher automation degree and discrimination accuracy.

The object of the present application is implemented by the following technical solution: a pancreatic postoperative diabetes prediction system based on supervised deep subspace learning, including a preoperative CT image data acquisition module, a residual pancreatic region of interest acquisition module, an image feature calculation module, a clinical feature calculation module and a deep subspace learning module.

The preoperative CT image data acquisition module is configured to acquire CT image data before a pancreatectomy, and input the CT image data into the residual pancreatic region of interest acquisition module and the image feature calculation module.

The residual pancreatic region of interest acquisition module is configured to input preoperative CT image data into a trained pancreas segmentation network to obtain a pancreas prediction region; in the pancreas prediction region, an excised edge of a pancreas is simulated by software to obtain a residual pancreatic region after the pancreatectomy, and input the residual pancreatic region, as a region of interest for a subsequent calculation of an image feature, into the image feature calculation module.

The image feature calculation module is configured to calculate a pancreatic image feature according to the preoperative CT image data and a region of interest of the image feature, and input the pancreatic image feature to the deep subspace learning module.

The clinical feature calculation module is configured to acquire clinical information related to postoperative diabetes of a patient, including demographic information, living habits, pancreatic volume resection rate, pancreatic residual volume and abdominal fat and muscle content features, perform feature concatenation to form a clinical feature, and input the clinical feature into the deep subspace learning module.

The deep subspace learning module is configured to perform feature dimensionality reduction and fusion through a deep subspace learning network. The deep subspace learning network includes an encoder, a latent spatial variable self-representative layer and a decoder, and for supervising a learning of the latent spatial variable self-representative layer; the deep subspace learning network inputs the pancreatic image feature and the clinical feature, outputs a latent spatial variable through the encoder, connects the latent spatial variable output by the encoder with a fully connected layer, and effects an activation function to obtain a predicted value of diabetes risk.

Further, the preoperative CT image data acquisition module truncates a HU value of the CT image data to [−100, 240] and then discretizes the value to [0,255] after acquiring the CT image data before the pancreatectomy, calculates a rectangular frame of a region surrounded by residual pancreas, sets an edge expansion value, and then truncates a rectangular frame of the CT image data and a residual pancreas labeled image.

Further, in the residual pancreatic region of interest acquisition module, a preoperative pancreatic CT image is automatically segmented based on the deep convolutional neural network to obtain a complete pancreas prediction region, and a surgical cutting plane is simulated in Medical Imaging Interaction Toolkit (MITK) software according to a surgical record or a tumor position, so as to obtain a resected residual pancreatic region as a residual pancreatic region of interest for the subsequent calculation of the image feature.

Further, in the residual pancreatic region of interest acquisition module, the pancreas segmentation network selects a densely connected dilated convolutional network.

Further, the image feature calculation module is configured to filter the preoperative CT image data, calculate a first-order statistical feature vector, a shape feature vector and a texture feature vector by using filtered images and the residual pancreatic region of interest, and concatenate the three feature vectors to obtain a filtered feature vector; according to the input of the fully connected layer of the trained pancreas segmentation network, a mean feature of all pixels in the residual pancreatic region of interest is calculated, and standardized to obtain a high-level semantic feature vector; and the filtered feature vector is concatenated with the high-level semantic feature vector to obtain the pancreatic image feature.

Further, feature vectors of all the filtered CT image data are processed as follows:

$$X_f = (X_f - \min(X_f))/(\max(X_f) - \min(X_f))$$

where, $X_f$ represents the feature vector, f represents a specific feature name, with a vector length being a number n of all filtered CT image data.

Further, the filtered feature vector is concatenated with the high-level semantic feature vector to obtain an image feature $X_{img}$:

$$X_{img} = concat(X_{radiomics}, X_{deep}), \text{axis} = 1)$$

where $X_{img} \in R^{d_1 \times n}$, $d_1$ represents a dimension of the image feature, n represents the number of CT image data, $X_{radiomics}$ represents the filtered feature vector, which represents a radiomics feature, and $X_{deep}$ represents the high-level semantic feature vector.

Further, the clinical feature calculation module includes a body composition feature calculation module, a clinical information feature calculation module and a pancreas resection feature calculation module.

The body composition feature calculation module is configured to calculate areas of visceral fat, subcutaneous fat and skeletal muscle in a cross-sectional image of a third vertebra position of CT volume data, and calculate a ratio of visceral fat to skeletal muscle and a ratio of visceral fat to subcutaneous fat to obtain a body composition feature.

The clinical information feature acquisition module is configured to acquire basic clinical information of the patient, including demographic features and living habits, and form a clinical information feature.

The pancreas resection feature calculation module is configured to calculate a preoperative volume and a postoperative volume of pancreas, calculate a pancreas resection ratio, and construct a pancreas resection feature.

Results of the body composition feature calculation module, the clinical information feature calculation module and the pancreas resection feature calculation module are concatenated to form the clinical feature, which is input into the deep subspace learning module.

Further, a loss function of the deep subspace learning network in the deep subspace learning module is:

$$L(\Theta) = \left\| X - \hat{X} \right\|_F^2 + 2Tr(X^T L \hat{X}) + \frac{1}{2}\gamma_1 \left\| Z - ZC \right\|_F^2 + \frac{\alpha}{2}\gamma_1 \|C\|_1 + \gamma_2 BCE(\hat{y}, y),$$

$$\text{s.t. diag}(C) = 0$$

where $X = \{X_{img}, X_{clinic}\}$, $X_{img}$ represents the image feature, $X_{clinic}$ represents the clinical feature, $\hat{X}$ represents an output of the decoder, y represents a real situation of the patient suffering from postoperative diabetes, $\hat{y}$ represents a diabetes risk predicted by a model, Z represents the latent spatial variable output by the encoder, L represents a Laplacian matrix, the symbol Tr represents the trace of the matrix, and the symbol T represents a matrix transposition, Θ represents all the parameters in the deep subspace learning network, including an encoder parameters $\Theta_e$, a self-representative coefficient matrix C, a supervision module parameter $\Theta_s$ and a decoder parameter $\Theta_d$; α, $\gamma_1$ and $\gamma_2$ are regularization coefficients, the symbol $\|\cdot\|_F$ represents a frobenius norm, and BCE(·) represents a cross entropy loss.

The present application has the beneficial effects that the preoperative CT images and clinical information are proposed to predict the risk of diabetes after pancreatectomy, and the blank of predicting the risk of diabetes by preoperative images is filled. Different from the traditional image genomics method, the present application proposes to automatically segment the preoperative CT image based on the deep convolutional neural network, and on this basis, simulate the cut edge of the pancreas to obtain the region of interest of the postoperative residual pancreas, which can greatly reduce the amount of manual labeling. Further, the present application establishes a high-dimensional image feature set that combines the radiomics features and high-level semantic features, and a clinical feature set related to diabetes, including pancreatectomy rate, fat and muscle tissue components, demographic information and living habits, which is the basis and key to mining the features related to diabetes after pancreatectomy. At the same time, a supervised deep subspace learning network is innovatively proposed to realize feature dimensionality reduction and fusion in the subspace, and at the same time, a prediction model is trained to mine sensitive features related to the prediction task, which improves the accuracy of the prediction model.

The pancreatic postoperative diabetes prediction system based on supervised deep subspace learning further includes a display device, which is configured to receive the predicted value of diabetes risk from the deep subspace learning module, and display the predicted value of diabetes risk to the user, so as to assist the user to determine the risk of diabetes after surgery.

DESCRIPTION OF EMBODIMENTS

The specific embodiment of that present invention will be further described in detail with reference to the accompanying drawing.

Figure 1:
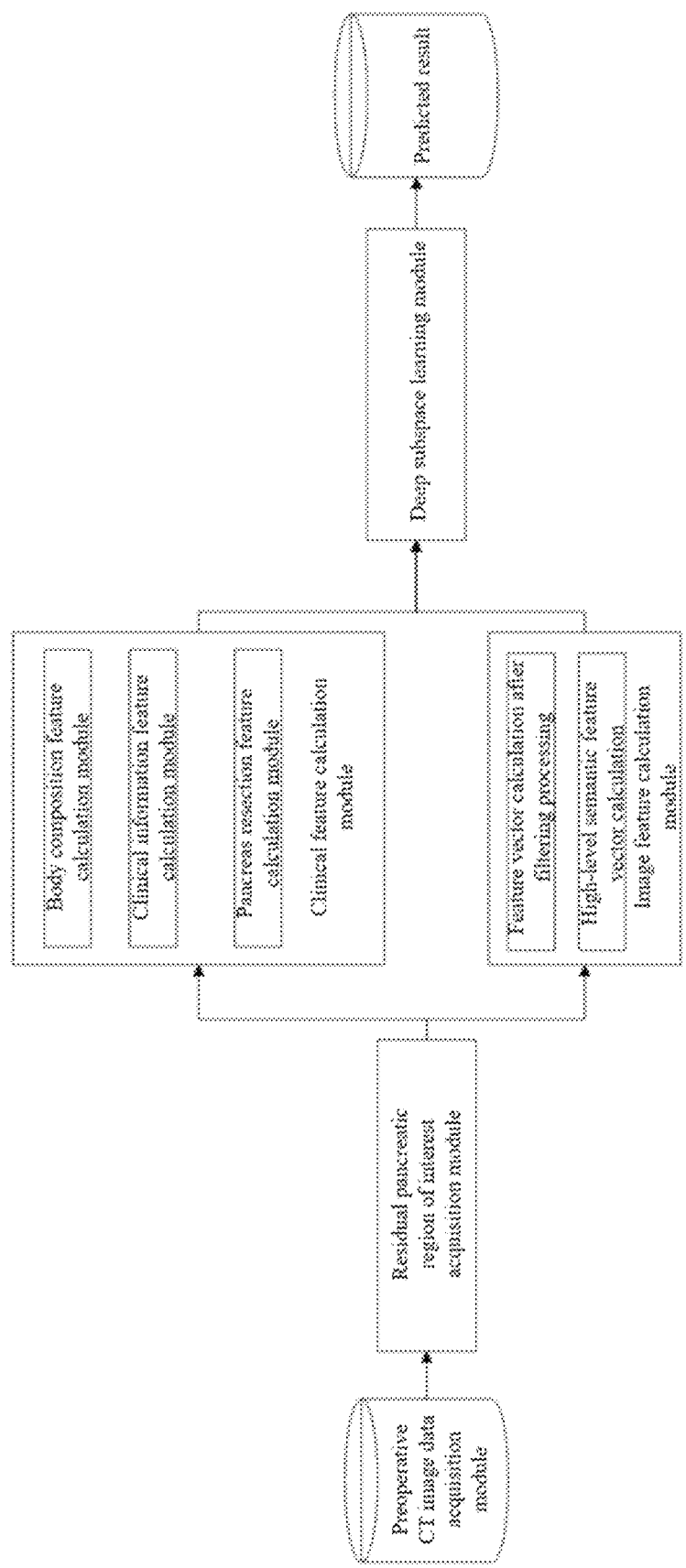
FIG. 1 is a diagram of a pancreatic postoperative diabetes prediction system based on supervised deep subspace learning of the present application.

As shown in FIG. 1, the object of the present application is to provide a diabetes risk prediction system after pancreatectomy based on supervised deep subspace learning, in view of the blank in predicting diabetes risk after pancreatectomy by using clinical features and preoperative image features, and the problems that the existing imaging methods rely on manual delineation of the region of interest, and the dimensionality reduction effect of high-dimensional features is not good and the discrimination ability is insufficient.

Figure 4:
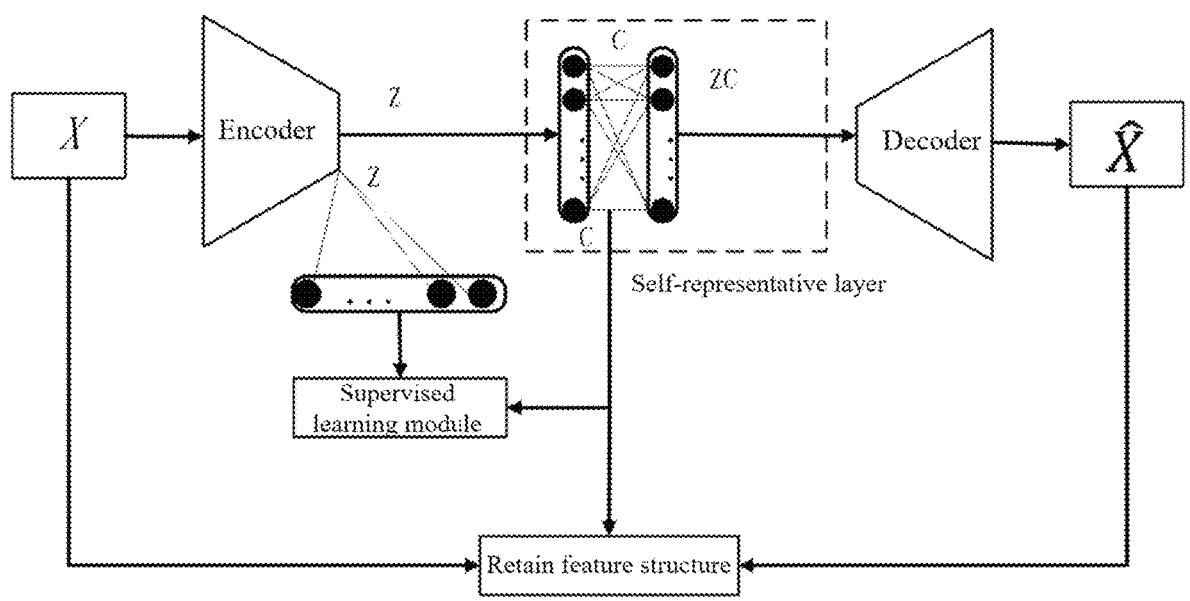
FIG. 4 is a schematic diagram of a supervised deep subspace learning network structure.

In the region-of-interest labeling stage, a pancreas prediction region is obtained by the residual pancreatic region-of-interest acquisition module. Specifically, a preoperative pancreatic CT image is automatically segmented based on a deep convolutional neural network to obtain a complete pancreas prediction region, and then a surgical cutting plane is simulated in a Medical Imaging Interaction Toolkit MITK software according to the surgical record or tumor position, so as to obtain a residual pancreatic region after pancreatectomy as the residual pancreatic region-of-interest for subsequent image feature calculation. In the feature extraction stage, the image feature calculation module is used to calculate the pancreatic image features. On the one hand, traditional image features such as first-order statistical features, shape features and high-order texture features are extracted from the image filtered by wavelet. On the other hand, the high-level semantic features of the residual pancreatic region are obtained based on a feature map output by the deep convolutional neural network, and the pancreatic image features are constructed. Further, clinical information related to postoperative diabetes of a patient is extracted by a clinical feature calculation module, including demographic information (gender, age, etc.), living habits (drinking, smoking, etc.), pancreatic volume resection rate, residual pancreatic volume and abdominal fat and muscle content, and a clinical feature set is established. In the feature selection stage, a supervised deep subspace learning network is established through the deep subspace learning module, and the supervised learning module is added to reduce and fuse the image features and clinical features to obtain their sparse representation in the low-dimensional subspace, from which a similarity matrix between features is calculated. The supervised learning module in the trained deep subspace learning network is used to predict the risk of postoperative diabetes. The deep subspace learning network used in the present application is shown in FIG. 4.

After the preoperative CT image data acquisition module acquires the CT image data before pancreatectomy, it preprocesses the CT image data and divides the data set, which is specifically as follows:

1) Resampling of CT images, discretization of gray values and frame selection of image regions. For a preoperative pancreatic CT image, its spatial resolution is resampled to 1*1*1 mm, and the HU value of the image is truncated to [−100, 240], and then discretized to [0,255]. The HU value, which is a CT value, is a measurement unit to measure the density of a local tissue or organ in a human body, and is usually called hounsfield unit (HU). Air is −1000, and the dense bone is +1000. Then, according to the residual pancreas, the rectangular frame of the area surrounding the residual pancreas is calculated, and the edge expansion value is set, and then the CT image and the rectangular frame of the labeled image are truncated. This step can reduce the amount of subsequent image feature calculation.

2) According to 50%, 20% and 30%, the patient queue after pancreatectomy is randomly divided into a training set $S_{tr}$, a verification set $S_{val}$ and a test set $S_{te}$. Whether the patient has diabetes after operation is regarded as the real label y of the prediction model, where y=1 indicates that the patient has diabetes or abnormal diabetes after the operation, and y=0 indicates that the patient's blood sugar function is normal.

Figure 2:
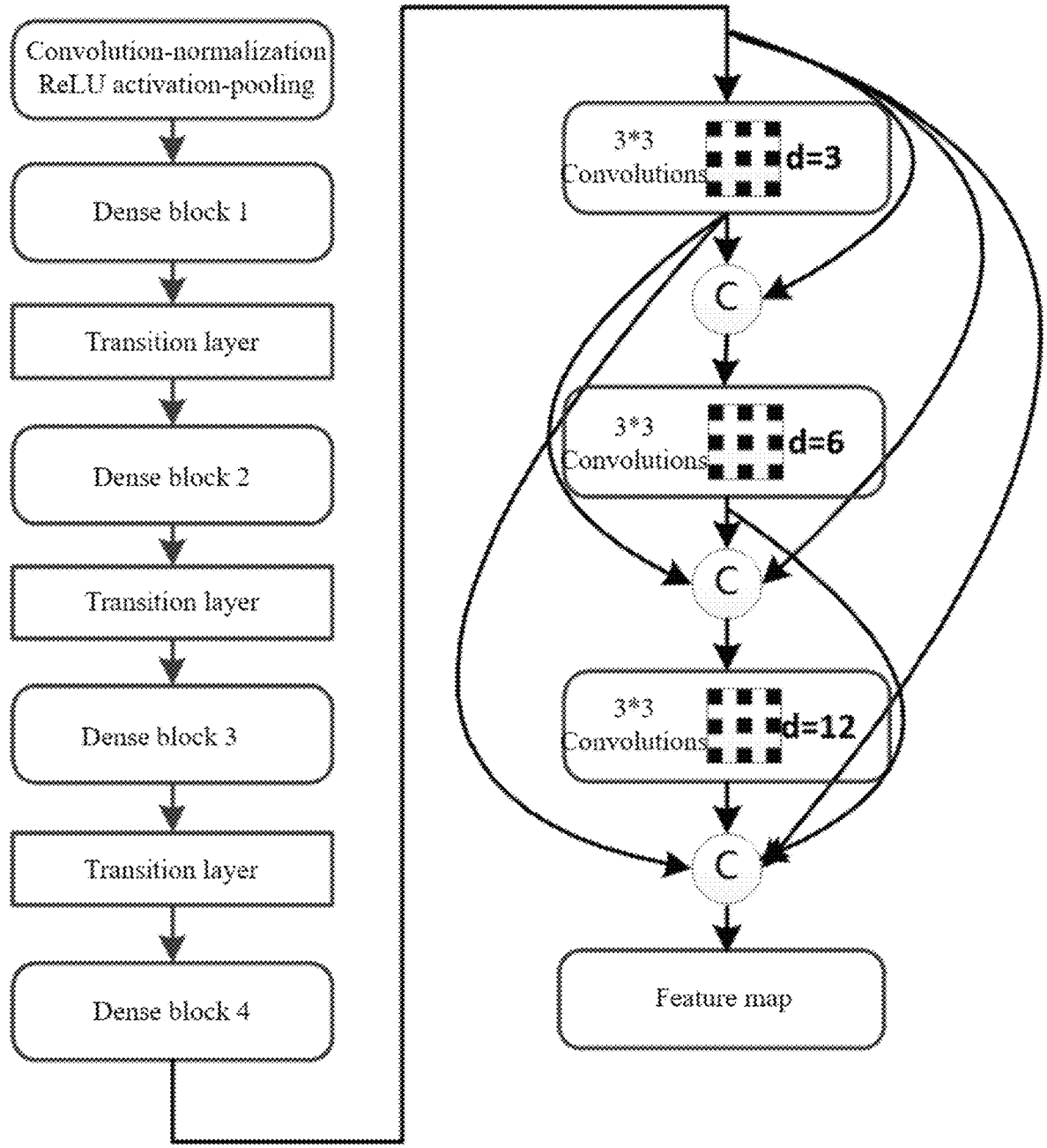
FIG. 2 is a schematic diagram of a densely connected expanded convolutional neural network architecture.

The residual pancreatic region of interest acquisition module is used for automatic segmentation of a pancreatic CT image and extraction of a residual pancreatic region of interest. Specifically, the preoperative pancreatic CT volume data is recorded as I with a size of 512×512×L, where L is the number of layers of the volume data. I is sliced in the axial plane to obtain a two-dimensional image sequence. Three consecutive images are combined into a three-channel pseudo-color image, which is recorded as $I_{A,l}$ (l=1, . . . , L). For each two-dimensional image $I_{A,l}$, contrast adjustment and image frame selection are carried out. Specifically, the HU value of the image is truncated to [−100, 240] and then normalized to [0,1]. For each two-dimensional image $I_{A,l}$, an image block with a size of 448×448 is truncated and input into the trained pancreas segmentation network to obtain the pancreas prediction region, which is recorded as $R_0$. The pancreas segmentation network can be a densely connected dilated convolutional network or other end-to-end full convolutional neural networks. In the present application, a densely connected dilated convolutional network DenseASPP is selected as the pancreas segmentation network. DenseASPP is a kind of generalized dense connection network, which has a densely connected AtrousSpatial Pyramid Pooling layer (ASPP). It encodes multi-scale information by connecting feature maps from atrous convolutions with different expansion rates. Compared with the original ASPP, DenseASPP uses the outputs densely connected to each atrous convolutional layer, and obtains more and more larger receptive fields at a reasonable expansion rate. Therefore, DenseASPP can obtain the output feature map covering a larger receptive field in a very dense way. The present application uses DenseNet161 followed by an atrous convolutional layer to construct a basic DenseASPP network (see FIG. 2). The first part of DenseASPP is a feature generation block, which outputs the basic feature map $y_0$ with a size of ⅛ of the input image. Specifically, it consists of a convolution layer, four dense blocks and three transition layers. The number of initial feature maps in the first dense block is 96, and the growth rate is 48. The second part of DenseASPP is a dense ASPP module built on the feature map $y_0$ by densely connected atrous convolutional layers, in which the number of atrous convolutional layers is 3, with expansion rates d of 3, 6 and 12 respectively.

On the pancreas prediction region that has been automatically segmented, according to the operation record or the location of pancreatic tumor, MITK software is used to simulate the edge of pancreatectomy, and the residual pancreatic region after resection is obtained, which is recorded as R as the residual pancreatic region of interest for subsequent image feature calculation.

The image feature calculation module uses the residual pancreatic region of interest to calculate the image features. Because the original images of most pancreatic regions are usually piecewise constant and contain highly redundant signals, the present application adopts wavelet analysis to extract high-frequency and low-frequency information of images. Wavelet analysis uses a wavelet function called wavelet to transform a signal into a spatial/frequency representation. After the wavelet transform, the image is decomposed into multi-resolution subspaces, and the corresponding wavelet coefficients reflect the high and low frequency signals of the original image. The CT image data before pancreatectomy is filtered by wavelet, and the wavelet bases are db1, db5, sym7, coif3 and haar respectively. A wavelet toolkit based on matlab decomposes the image into high-frequency and low-frequency signals in three directions. Specifically, the high-frequency and low-frequency information of the image is decomposed by using wavedec3 in the wavelet toolkit. 3D wavelet transform can be expressed as $$V^3 = (L^x \oplus H^x) \otimes (L^y \oplus H^y) \otimes (L^z \oplus H^z) = L^x L^y L^z \oplus L^x H^y L^z \oplus$$
$$H^x L^y L^z \oplus H^x H^y L^z \oplus L^x L^y H^z \oplus L^x H^y H^z \oplus H^x L^y H^z \oplus H^x H^y H^z,$$

where $\oplus$ and $\otimes$ represent addition and convolution operations, respectively. H and L represent high-pass filtering and low-pass filtering respectively, and x, y and z represent three-dimensional coordinate axes.

Under each group of wavelet bases, a total of 8 decomposition coefficients (LLL, LLH, LHL, LHH, HLL, HLH, HHL, HHH) can be obtained. A total of 40 groups of filtered images can be obtained. By using the image filtered by wavelet and the residual pancreatic region of interest, the first-order statistical features, shape features and texture features (GLCM, GLRLM, NGTDM, GLDM) are calculated based on a Pyradiomics toolkit. See Table 1 for the specific feature names of various features, and 85 features can be calculated for each filtered image. The calculated feature vector is recorded as $X_f$, where f represents a specific feature name. Finally, 3400-dimensional features are obtained.

TABLE 1

Image Feature Names

| Category of features | Number of features | Name of features |
|---|---|---|
| First-order statistical features | 18 | 10Percentile, 90Percentile, Energy, Entropy, TotalEnergy, InterquartileRange, Kurtosis, Minimum, Maximum, Mean, Median, Range, MeanAbsoluteDeviation (MAD), RobustMeanAbsoluteDeviation(RAD), RootMeanSquared (RMS), Skewness, Variance, Uniformity |
| Shape feature | 10 | Maximum2DDiameterColumn (Max 2D d Column), Maximum2DDiameterRow (Max 2D d Row), Maximum2DDiameterSlice (Max 2D d Slice), Maximum3DDiameter (Max 3D d), Mesh Volume, Sphericity, SurfaceArea, Surface VolumeRatio |
| GLCM | 22 | Autocorrelation, JointAverage, ClusterProminence, ClusterShade, ClusterTendency, Contrast, Correlation, Difference Average, DifferenceEntropy, Difference Variance, JointEnergy, JointEntropy, Imc1, Imc2, Idm, Idn, Inverse Variance, MaximumProbability, SumEntropy, SumSquares. |
| GLRLM | 16 | GrayLevelNonUniformity, GrayLevelNonUniformityNormalized, GrayLevel Variance, HighGrayLevelRunEmphasis, LongRunEmphasis, LongRunHighGrayLevelEmphasis, LongRunLowGrayLevelEmphasis, LowGrayLevelRunEmphasis, RunEntropy, RunLengthNonUniformity, RunLengthNonUniformityNormalized, RunPercentage, Run Variance, ShortRunEmphasis, ShortRunHighGrayLevelEmphasis, ShortRunLowGrayLevelEmphasis. |
| NGTDM | 5 | Coarseness, Complexity, Contrast, Strength, Busyness. |
| GLDM | 14 | DependenceEntropy, DependenceNonUniformity, DependenceNonUniformityNormalized, Dependence Variance, GrayLevelNonUniformity, GrayLevelVariance, HighGrayLevelEmphasis, LargeDependenceEmphasis, |

TABLE 1-continued

Image Feature Names

| Category of features | Number of features | Name of features |
|---|---|---|
| | | LargeDependenceHighGrayLevelEmphasis, LargeDependenceLowGrayLevelEmphasis, LowGrayLevelEmphasis, SmallDependenceEmphasis, SmallDependenceHighGrayLevelEmphasis, SmallDependenceLowGrayLevelEmphasis. |

Then, the input of the fully connected layer of the pancreas segmentation network is extracted as a high-level semantic feature, and the mean value of features of all pixels in the residual pancreatic region of interest is calculated. In this application, a densely connected dilated convolutional network (DenseASPP) is selected as the pancreas segmentation network, and the contrast of CT image data before pancreatectomy is adjusted and then input into the trained segmentation network. Through the forward propagation of the network, the input of the last fully connected layer output by the network is taken as the extracted high-level semantic feature, and the average value of all pixels in the region of interest is calculated, finally obtaining a 1488-dimensional feature.

The image features of all CT image data are stretched to the range of [0,1], that is $(X_f=(X_f-\min(X_f))/(\max(X_f)-\min(X_f))$, where $X_f$ represents a feature vector, and the vector length is the number n of all CT image data. The wavelet-based feature vector is concatenated with the high-level semantic feature vector to get an image feature $X_{img}$=concat $(X_{radiomics}, X_{deep})$, axis=1). $X_{img} \in R^{d_1 \times n}$, $d_1$ is the dimension of the image feature, and n is the number of CT image data, $X_{radiomics}$ is the feature vector after filtering, which represents a radiomics feature, and $X_{deep}$ is the high-level semantic feature vector.

The clinical feature calculation module includes a body composition feature calculation module, a clinical information feature calculation module and a pancreas resection feature calculation module.

Figure 3:
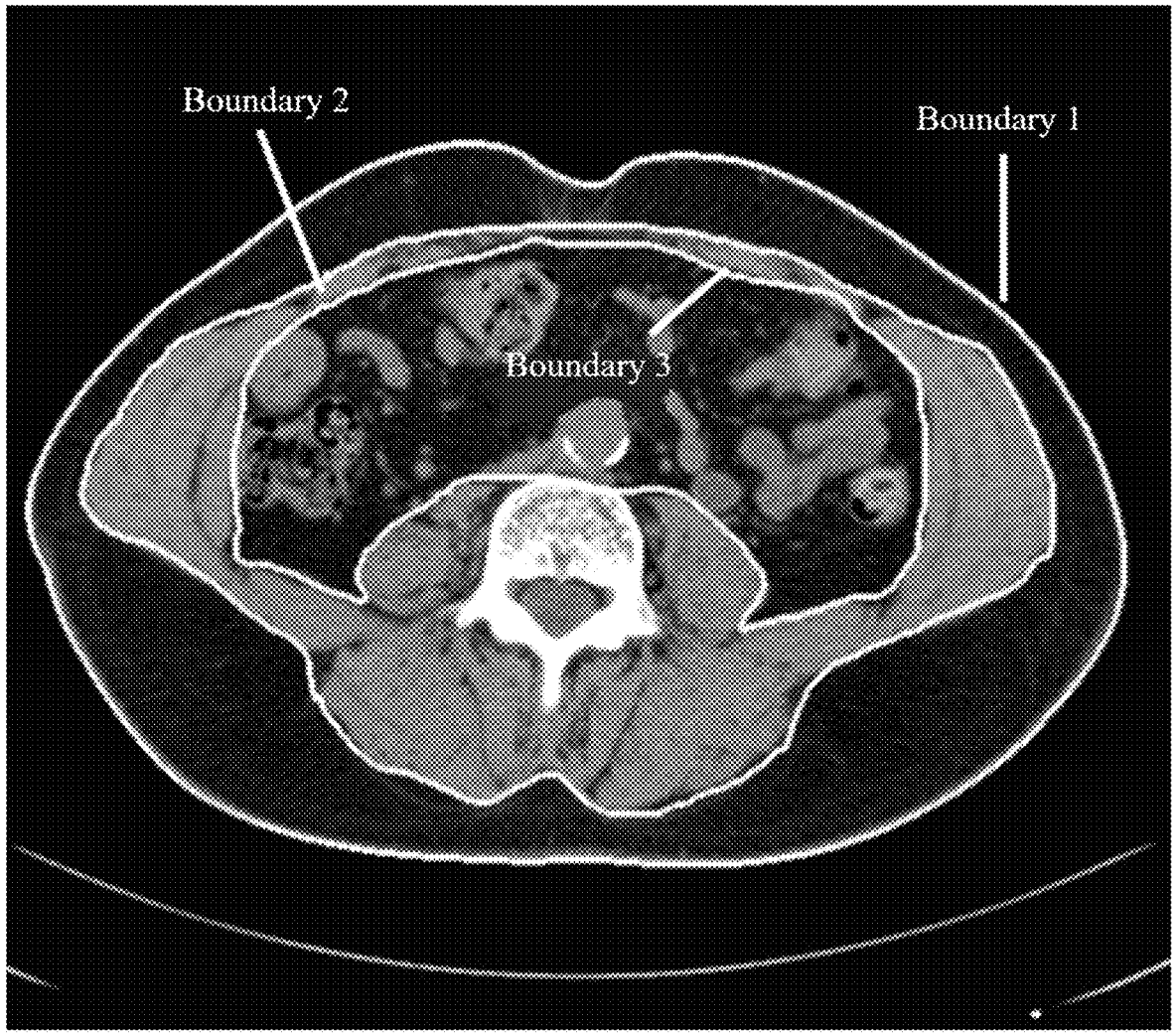
FIG. 3 is a schematic diagram of the boundaries of a body composition.

The body composition feature calculation module extracts the cross-sectional image of the third vertebra position of CT volume data, and manually labels the body peripheral boundary 1, the subcutaneous fat and skeletal muscle boundary 2, and the skeletal muscle and abdominal cavity boundary 3 (see FIG. 3). The area of the regions of the visceral fat, subcutaneous fat and skeletal muscle is calculated according to the CT HU values. Specifically, the HU value range of the adipose tissue is [−190. −30], the HU value range of the muscle tissue is [−29, 150], and the area between boundary 1 and boundary 2 is the location of subcutaneous fat. According to the HU value range of the adipose tissue, a threshold is set to extract the subcutaneous adipose tissue region SAT. The region within boundary 3 is the region where visceral fat is located. According to the HU value range of the adipose tissue, a threshold is set to extract a visceral adipose tissue region VAT. The region between boundary 2 and boundary 3 is the location of skeletal muscle. According to the HU value range of muscle, a skeletal muscle region SKM is extracted. For the three tissue regions extracted above, the area $S_i$, $i \in \{SAT, VAT, SKM\}$ and a total fat area $S_{AT}=S_{VAT}+S_{SAT}$ are calculated. In addition, the ratio $S_{VAT}/S_{SKM}$ of visceral fat to skeletal muscle and the ratio $S_{VAT}/S_{SAT}$ of visceral fat to subcutaneous fat are calculated. The body composition feature is $$X_{composition}=\{S_{VAT}, S_{SAT}, S_{SKM}, S_{VAT}/S_{SAT}, S_{VAT}/S_{SKM}, S_{AT}\}.$$

The clinical information feature acquisition module acquires basic clinical information of a patient, including demographic features (gender, age, etc.) and living habits (smoking, drinking, etc.) to form the clinical information feature $X_{info}$.

The pancreas resection feature calculation module calculates the preoperative volume of the pancreas and the postoperative volume of the pancreas according to the pancreas prediction region and the residual pancreatic region of interest, calculates the pancreas resection ratio resect_rate=$(V_0-V_1)/V_0$, and constructs a pancreas resection feature $X_{resect}=\{(V_0-V_1)/V_0, V_1\}$.

The results of the body composition feature calculation module, the clinical information feature calculation module and the pancreas resection feature calculation module are concatenated to form the clinical features, that is, $X_{clinic}=\{X_{composition}, X_{info}, X_{resect}\}$, $X_{clinic} \in R^{d_2 \times n}$, $d_2$ is dimension of the clinical feature.

There are highly redundant or irrelevant features in the above-mentioned image feature set and clinical feature set, therefore feature dimensionality reduction is needed. At the same time, the image feature and clinical feature need to be fused. According to the present application, a deep subspace learning process is carried out through the deep subspace learning module, and feature dimensionality reduction and fusion are realized.

The deep subspace learning module includes a deep subspace learning network based on a self-encoder, and the specific construction process is as follows: first, a self-encoder network AE is designed. An ordinary self-encoder is generally composed of an encoder and a decoder. Through unsupervised learning, it learns the efficient representation of input data. This efficient representation of input data is called codings, and its dimension is generally much smaller than that of input data, so that the self-encoder can be used for dimensionality reduction. In the present application, in order to realize subspace clustering by using the self-encoder, the present application also adds a latent spatial variable self-representative layer to the encoder. Therefore, the AE designed in this invention consists of an encoder E, a decoder D and a latent spatial variable self-representative layer. The encoder E includes three convolutional layers-activation layers, the decoder D consists of three corresponding convolutional layers-activation layers, and the latent spatial variable self-representative layer includes a fully connected layer. Then, a supervised learning module is added to the self-encoder network, that is, a fully connected layer is connected to a latent spatial variable Z output by the encoder, and effects an activation function to obtain the predicted value of the label.

The data input into the deep subspace learning network is recorded as $X=\{X_{img}, X_{clinic}\}$, and it is output as a latent spatial variable $Z=E_{\Theta_e}(X)$ through the encoder E, where $\Theta_e$ is an encoder parameter, and then it is output by the decoder as $\hat{X}=D_{\Theta_d}(E_{\Theta_e}(X))$, $\Theta_d$ is a decoder parameter. S is recorded as a similarity matrix describing the similarity between data, in which the element $S_{ij}$ of the similarity matrix represent the coefficient that the data $X_i$ can be represented by the reconstructed data $\hat{X}_j$. In order to make the difference between the reconstructed data $\hat{X}$ after encoding and decoding and the original data X as small as possible, the reconstruction loss of the network is defined.

$$L_0 = \sum_{ij} S_{ij} \|X_i - D_{\Theta_d}(E_{\Theta_e}(X_j))\|^2 = Tr\left[(X-\hat{X})^T D(X-\hat{X})\right] + 2Tr(X^T L \hat{X})$$

where $D = \text{diag}(\Sigma_{j=1}^n S_{ij})$ is a diagonal matrix, $L = D - S$ is a Laplacian matrix. The symbol Tr represents the trace of the matrix, the symbol T represents the matrix transposition, the symbol diag($\cdot$) represents the diagonal matrix, and n represents the number of samples.

In subspace clustering, it is assumed that a sample can be linearly represented by the dictionary of the data itself, that is, $$X = XZ, \text{ s.t. } \text{diag}(Z) = 0,$$

where $Z \in \mathcal{R}^{n \times n}$ is a representation matrix. Then, the similarity graph describing the data relationship can construct a similarity matrix $$S = \frac{|Z| + |Z^T|}{2}.$$

Because the relationship between high-dimensional data may be nonlinear and cannot be expressed by linear relationship, the present application first projects data X into the latent space through the encoder in the self-encoder, and it is deemed that the data representation Z in the low-dimensional latent space can be expressed linearly by itself. At the same time, this representation is required to be sparse. Therefore, the loss function of the self-representative layer can be defined as $$L_1 = \alpha \|C\|_1 + \frac{1}{2} \|Z - ZC\|_F^2, \text{ s.t. } \text{diag}(C) = 0.$$

where the similarity matrix S is calculated from the self-representative coefficient matrix C, and the calculation formula is $$S = \frac{1}{2}(|C| + |C|^T).$$

The first term of the loss function formula requires that the coefficient matrix C is sparse, that is, the screened features are sparse. The second term requires that the data in the same subspace can be self-represented, that is, it can be linearly represented by other data in the same subspace. The symbol $\|\cdot\|_1$ represents a L1 norm, the symbol $\|\cdot\|_F$ represents a frobenius norm and $\alpha$ represents a regularization coefficient.

The above matrix D is normalized, and the normalized diagonal matrix is recorded as $D_n = I$, and the corresponding normalized Laplacian matrix is $L_n = D^{-1/2} L D^{1/2}$, which is substituted into $L_0$, and $L_0$ can be re-expressed as $$L_0 = \|X - \hat{X}\|_F^2 + 2Tr(X^T L \hat{X}).$$

The traditional self-encoder learning method is unsupervised. In order to strengthen the specificity of the selected features, a supervised learning module is introduced into the self-encoder. The parameter of the fully connected layer introduced is recorded as $\theta_s$, the activation function is a softmax function $\sigma$, and the latent spatial variable Z passes through the fully connected layer and the activation function to get $\hat{y} = \sigma \circ f_{\theta_s}(Z)$, the real label of the data is recorded as y, and the loss function of the supervised learning module is expressed as $$L_3 = BCE(\hat{y}, y)$$

where BCE($\cdot$) represents a cross entropy loss.

To sum up, the loss function of the deep subspace learning network is defined as $$L(\Theta) = \|X - \hat{X}\|_F^2 + 2Tr(X^T L \hat{X}) + \frac{1}{2}\gamma_1 \|Z - ZC\|_F^2 + \frac{\alpha}{2}\gamma_1 \|C\|_1 + \gamma_2 BCE(\hat{y}, y), \text{ s.t. } \text{diag}(C) = 0.$$

where $\Theta$ represents all the parameters in the network, including a self-encoder parameter $\Theta_e$, a self-presentation layer parameter C, a supervision module parameter $\Theta_s$ and a decoder parameter $\Theta_d$. $\alpha$, $\gamma_1$ and $\gamma_2$ are regularization coefficients.

Using a training set $S_{tr}$ and a verification set $S_{val}$, the parameters of network structure and model are set based on a grid search method, including the number of neurons, the number of layers of the network, learning rate, batchsize, iteration steps, regularization coefficient $\gamma_1$ and $\gamma_2$. The subspace learning network is trained by the divided training set $S_{tr}$, and the network parameters are optimized by the ADAM method. Finally, the trained deep subspace learning network model is obtained.

The test data X_tt is input into the subspace learning network model, to obtain the representation Z and the self-representation ZC of the data in the low-dimensional subspace. By using the supervised learning module in the subspace learning network, the category of ZC is predicted and the predicted value $\hat{y}_{tt}$ is obtained. $\hat{y}_{tt}$ is compared with the label $y_{tt}$ for ROC analysis. Cut-off points are determined at the point with the maximum positive likelihood ratio on the ROC curve, the sensitivity, specificity, area under the ROC curve (AUC) are calculated, and the accuracy of the pathological reaction is evaluated. The greater the AUC value, the higher the evaluation accuracy of the system of the present application.

Specific application example: a pancreas tail resection cohort was established, including data of 212 patients, among which 65 patients suffered with postoperative diabetes. The basic features of the patients were extracted from preoperative CT images and electronic medical records. The method was verified on the cohort by using a 5-fold cross-validation method. All the data were divided into five parts, numbered 1, 2, 3, 4 and 5. The first group of experiments used the numbers 2, 3, 4 and 5 for training, 1 for testing, the second group of experiments used 1, 3, 4 and 5 for training, 2 for testing, and so on. Finally, the accuracies of the five groups of experiments are averaged. The data were processed according to the following steps:

1. Image processing. The pancreatic region in the CT image was segmented by a densely connected dilated convolutional network. Then MITK software was used to simulate the pancreatic margin, and the residual pancreatic region of interest after operation was obtained.

2. Feature calculation. Aiming at the residual pancreatic region of interest, the image feature based on wavelet filtering and high-level semantic feature based on deep learning were calculated to form an image feature set. The body composition feature and pancreas resection feature were calculated, and the clinical information of the patients was extracted to form a clinical feature set.

3. The data of the training set were input into the subspace learning network to train the network model.

4. The test data were input into the subspace learning network to obtain the predicted risk value of diabetes.

The results of 5-fold cross-validation show that the features selected by the subspace learning network include 36 image features and 4 clinical features. the clinical features include drinking, muscle content, age and residual pancreatic volume. The image features include 9 db5 filtering features, 8 sym7 filtering features and 19 haar filtering features. The accuracy of the prediction model of diabetes risk for patients after pancreatectomy is AUC=0.824. According to the method, the image features and clinical features are jointly mined, and the mined clinical variables are consistent with the related factors reported in the literature, which shows the effectiveness of the method for screening diabetes-related risk factors.

The above-mentioned embodiments are used to explain, but not to limit the present application. Any modification and change made to the present application within the scope of protection of the spirit and claims of the present application shall fall within the scope of protection of the present application.

In this application, the term "controller" and/or "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components (e.g., op amp circuit integrator as part of the heat flux data module) that provide the described functionality; or a combination of some or all of the above, such as in a system-on-chip.

The term memory is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

What is claimed is:

1. A pancreatic postoperative diabetes prediction system based on supervised deep subspace learning, comprising a preoperative CT image data acquisition module, a residual pancreatic region of interest acquisition module, an image feature calculation module, a clinical feature calculation module and a deep subspace learning module;
   wherein the preoperative CT image data acquisition module is configured to acquire CT image data before a pancreatectomy, and input the CT image data into the residual pancreatic region of interest acquisition module and the image feature calculation module;
   wherein the residual pancreatic region of interest acquisition module is configured to input preoperative CT image data into a trained pancreas segmentation network to obtain a pancreas prediction region; in the pancreas prediction region, an excised edge of a pancreas is simulated by software to obtain a residual pancreatic region after the pancreatectomy, and input the residual pancreatic region, as a region of interest for a subsequent calculation of an image feature, into the image feature calculation module;
   wherein the image feature calculation module is configured to calculate a pancreatic image feature according to the preoperative CT image data and a region of interest of the image feature, and input the pancreatic image feature to the deep subspace learning module;
   wherein the clinical feature calculation module is configured to acquire clinical information related to postoperative diabetes of a patient, comprising demographic information, pancreatic volume resection rate, pancreatic residual volume and abdominal fat and muscle content features, perform feature concatenation to form a clinical feature, and input the clinical feature into the deep subspace learning module; and
   wherein the deep subspace learning module is configured to perform feature dimensionality reduction and fusion through a deep subspace learning network, the deep subspace learning network comprises an encoder, a latent spatial variable self-representative layer and a decoder, and for supervising a learning of the latent spatial variable self-representative layer; the deep subspace learning network inputs the pancreatic image feature and the clinical feature, outputs a latent spatial variable through the encoder, connects the latent spatial variable output by the encoder with a fully connected layer, and effects an activation function to obtain a predicted value of diabetes risk; a loss function of the deep subspace learning network in the deep subspace learning module is:

$$L(\Theta) = \|X - \hat{X}\|_F^2 + 2Tr(X^T L \hat{X}) + \frac{1}{2}\gamma_1 \|Z - ZC\|_F^2 + \frac{\alpha}{2}\gamma_1 \|C\|_1 + \gamma_2 BCE(\hat{y}, y), \text{ s.t. } \text{diag}(C) = 0$$

where $X = \{X_{img}, X_{clinic}\}$, $X_{img}$ represents the image feature, $X_{clinic}$ represents the clinical feature, $\hat{X}$ represents an output of the decoder, y represents a real situation of the patient suffering from postoperative diabetes, $\hat{y}$ represents a diabetes risk predicted by a model, Z represents the latent spatial variable output by the encoder, L represents a Laplacian matrix, a symbol Tr represents a trace of a matrix, and a symbol T represents a matrix transposition, $\Theta$ represents all parameters in the deep subspace learning network, comprising an encoder parameter $\Theta_e$, a self-representative coefficient matrix C, a supervision module parameter $\Theta_s$ and a decoder parameter $\Theta_d$; $\alpha$, $\gamma_1$ and $\gamma_2$ are regularization coefficients, a symbol $\|\cdot\|F$ represents a frobenius norm, and BCE(·) represents a cross entropy loss.

2. The pancreatic postoperative diabetes prediction system based on supervised deep subspace learning according to claim 1, wherein the preoperative CT image data acquisition module truncates a HU value of the CT image data to [−100, 240] and discretizes the HU value to [0,255] after acquiring the CT image data before the pancreatectomy, calculates a rectangular frame of a region surrounded by residual pancreas, sets an edge expansion value, and truncates a rectangular frame of the CT image data and a residual pancreas labeled image.

3. The pancreatic postoperative diabetes prediction system based on supervised deep subspace learning according to claim 1, wherein in the residual pancreatic region of interest acquisition module, a preoperative pancreatic CT image is automatically segmented based on the deep convolutional neural network to obtain a complete pancreas prediction region, and a surgical cutting plane is simulated in Medical Imaging Interaction Toolkit (MITK) software according to a surgical record or a tumor position, in such a manner to obtain a resected residual pancreatic region as a residual pancreatic region of interest for the subsequent calculation of the image feature.

4. The pancreatic postoperative diabetes prediction system based on supervised deep subspace learning according to claim 3, wherein in the residual pancreatic region of interest acquisition module, the trained pancreas segmentation network selects a densely connected dilated convolutional network.

5. The pancreatic postoperative diabetes prediction system based on supervised deep subspace learning according to claim 1, wherein the image feature calculation module is configured to filter the preoperative CT image data, calculate a first-order statistical feature vector, a shape feature vector and a texture feature vector by using filtered images and the residual pancreatic region of interest, and concatenate the first-order statistical feature vector, the shape feature vector and the texture feature vector to obtain a filtered feature vector; according to an input of the fully connected layer of the trained pancreas segmentation network, a mean feature of all pixels in the residual pancreatic region of interest is calculated and standardized to obtain a high-level semantic feature vector; and the filtered feature vector is concatenated with the high-level semantic feature vector to obtain the pancreatic image feature.

6. The pancreatic postoperative diabetes prediction system based on supervised deep subspace learning according to claim 5, wherein feature vectors of all filtered CT image data are processed as follows:

$$X_f = (X_f - \min(X_f))/(\max(X_f) - \min(X_f))$$

where $X_f$ represents the feature vector, f represents a specific feature name, with a vector length being a number n of all CT image data.

7. The pancreatic postoperative diabetes prediction system based on supervised deep subspace learning according to claim 6, wherein the filtered feature vector is concatenated with the high-level semantic feature vector to obtain an image feature $X_{img}$:

$$X_{img} = concat(X_{radiomics}, X_{deep}), \text{axis} = 1)$$

where $X_{img} \in R^{d_1 \times n}$, $d_1$ represents a dimension of the image feature, n represents a number of CT image data, $X_{radiomics}$ represents the filtered feature vector, and further represents a radiomics feature, and $X_{deep}$ represents the high-level semantic feature vector.

8. The pancreatic postoperative diabetes prediction system based on supervised deep subspace learning according to claim 1, wherein the clinical feature calculation module comprises a body composition feature calculation module, a clinical information feature calculation module and a pancreas resection feature calculation module;

wherein the body composition feature calculation module is configured to calculate areas of visceral fat, subcutaneous fat and skeletal muscle in a cross-sectional image of a third vertebra position of CT volume data, and calculate a ratio of visceral fat to skeletal muscle and a ratio of visceral fat to subcutaneous fat to obtain a body composition feature;

wherein the clinical information feature acquisition module is configured to acquire basic clinical information of the patient, comprising demographic features, and form a clinical information feature;

wherein the pancreas resection feature calculation module is configured to calculate a preoperative volume and a postoperative volume of pancreas, calculate a pancreas resection ratio, and construct a pancreas resection feature; and wherein results of the body composition feature calculation module, the clinical information feature calculation module and the pancreas resection feature calculation module are concatenated to form the clinical feature, and the clinical feature is input into the deep subspace learning module.

\* \* \* \* \*